United States Patent [19]

Massaroli

[11] 4,311,702

[45] Jan. 19, 1982

[54] IMIDAZO[1,2-a]PYRIDINES HAVING ANTI-ULCER ACTIVITY

[75] Inventor: Giangiacomo Massaroli, Milan, Italy

[73] Assignee: Poli Industria Chimica S.p.A., Milan, Italy

[21] Appl. No.: 202,055

[22] Filed: Oct. 30, 1980

[30] Foreign Application Priority Data

Nov. 14, 1979 [IT] Italy ............................... 27292 A/79

[51] Int. Cl.³ .................. A61K 31/435; C07D 471/04
[52] U.S. Cl. ...................................... 424/256; 546/121
[58] Field of Search ......................... 546/121; 424/256

[56] References Cited

PUBLICATIONS

Migrdichian, Organic Synthesis, vol. 1, Reinhold Publishing Co., (1957), p. 409.

*Primary Examiner*—John M. Ford
*Assistant Examiner*—Bernard Dentz
*Attorney, Agent, or Firm*—Michael J. Striker

[57] ABSTRACT

Imidazo[1,2-a]pyridine of the formula

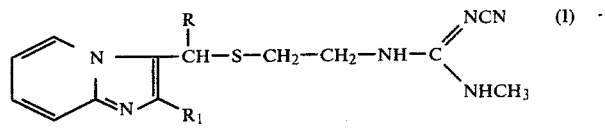

in which R represents H or $CH_3$ and $R_1$ represents H or $CH_3$ which can be used in human therapy as inhibitors of gastric secretion. The compounds are prepared by reacting a methylisothiourea of the formula

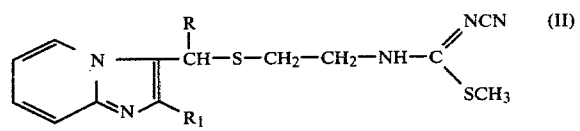

with methylamine in aqueous solution of dimethyl formamide or in hydroalcoholic solution, at temperatures between 0° and 50° C.

6 Claims, No Drawings

IMIDAZO[1,2-a]PYRIDINES HAVING ANTI-ULCER ACTIVITY

This invention relates to a series of imidazo [1,2-a] pyridines of general formula I

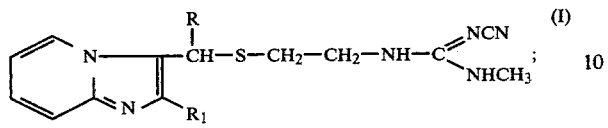

where R represents H or $CH_3$ and $R_1$ represents H or $CH_3$ and a process for their preparation, consisting in making a methyl isothiourea of formula II

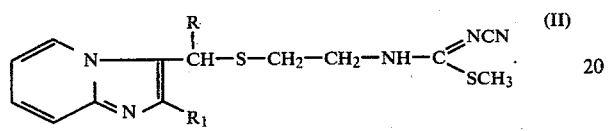

(where R and $R_1$ have the above indicated meanings) react with methylamine in aqueous solution of dimethylformamide or in hydroalcoholic solution. The compounds of the present invention can be used in human therapy as inhibitors of the gastric secretion.

The alcoholic component of the above mentioned hydroalcoholic solutions is preferably methanol, ethanol or isopropanol. The reaction is effected at temperature comprised between 0° and 50°, preferably at 25°.

Table I summarizes the main data relevant to the preparation and simple analysis of the compounds of formula I.

TABLE 1

| Compound | R | $R_1$ | % yield | reaction solvent | crystallization solvent | M.P. | N% calc. | N% found | S% calc. | S% found |
|---|---|---|---|---|---|---|---|---|---|---|
| Ia | H | H | 67 | DMF—$H_2O$ | EtOH | 185–187° | 29,14 | 28,96 | 11,02 | 10,98 |
| Ib | H | $CH_3$ | 55 | EtOH—$H_2O$ | MeOH—$H_2O$ | 214–216° | 27,79 | 27,44 | 10,60 | 10,47 |
| Ic | $CH_3$ | H | 63 | DMF—$H_2O$ | EtOH | 161–163° | 27,79 | 27,88 | 10,60 | 10,71 |
| Id | $CH_3$ | $CH_3$ | 82 | EtOH—$H_2O$ | EtOH | 183–184° | 26,56 | 26,31 | 10,13 | 9,98 |

The compounds of formula I object of the present invention are endowed with interesting gastric antisecretory and anti-ulcer activity, evidenced by various pharmacological tests chosen among those more commonly used to determine the above mentioned kind of pharmacological activity and more precisely:

cold and restraint gastric ulcers induced in the rat following the under mentioned method originally described by E. C. Senay and R. J. Levine in Proc. Soc. Exp. Biol. Med. 124 1221 (1967).

Wistar female rats fasting from the previous evening are introduced in plastic tubes having such a diameter to exert a light constriction and immediately after they are put in a thermoregulated ambient at about 4° C. Two hours later the rats are sacrificed under ethereal anesthesia and their stomachs are examined to ascertain the presence of ulcers.

The ulcer index of each stomach is determined, multiplying the number of gastric lesions of any kind by a corresponding arbitrary value (petechiae=0.5; punctiform ulcer=1; linear ulcer<2 mm=2; linear ulcer>2 mm=3) and adding the partial scores. Rats are treated with the compound under study half an hour before cold exposure. The anti-ulcer activity of the compounds of the present invention resulting from such test is indicated in Table 2 as ED50 that is the dose capable of reducing the ulcer index by 50% compared with controls.

acetylsalicylic acid and pylorus ligation gastric ulcers, induced in the rat following the undermentioned method described by S. Okabe, Y. Takata, K. Takeychi, T. Nagasuma, K. Takagi in Digestive Diseases 21, 618 (1976). Wistar male rats, weighing 160–200 g, fasting from the previous evening are administered intraduodenum with the compound under study immediately after pylorus ligation under light ethereal anesthesia. Two hours after treatment rats receive orally 50 mg/kg of acetylsalicylic acid, dissolved in 5% gum arabic solution. An hour later rats are sacrificed under ether anesthesia and stomachs examined for presence of ulcers. The anti-ulcer activity of the compounds of the present invention resulting from such test is illustrated in Table 2 as ED50 that is the dose reducing the number of ulcers by 50% compared with controls.

indomethacin gastric ulcers, induced in the rat following the under mentioned method originally described by Y. H. Lee, K. W. Mollison, W. C. Cheng in Arch. Int. Pharmacodyn. 192, 370 (1971).

Wistar male rats, weighing 160–200 g, starved for 24 hours, are administered endoperitoneally with 30 mg/kg of indomethacin in 0.6% aqueous suspension of 1% gum arabic solution and immediately after they are treated orally with the compound under study. 5 hours later animals are sacrificed under ethereal anesthesia, the stomachs are removed, open along the great curvature and examined for the presence of ulcers. The ulcer index is expressed in terms of square root of the number of gastric ulcers. The anti-ulcer activity of the compounds of the present invention resulting from such test is indicated in Table 2 as ED 50, that is the dose reducing the ulcer index by 50% in comparison with controls.

activity on gastric secretion, studied in "Shay" rats, following the below described method, originally reported by H. Shay, S. A. Komarov, S. S. Fels, D. Meranze, M. Grusenstein, H. Siplet in Gastroenterology 5, 43 (1945). Wistar male rats, weighing 160–200 g, starved for 24 hours are treated orally with the compound under study after pylorus ligation under light ethereal anesthesia. 4 hours later rats are anesthetized with ether and after oesophagus ligation, the stomachs are removed and the contents collected. After centrifugation of the gastric juice, the quantity of hydrochloric acid is determined by titration with 0.01 N Sodium hydroxide, using phenolphthalein as indicator. The antisecretory activity of the compounds object of the present invention evidenced in the above described test is indicated in Table 2 as ED50, that is the dose reducing the secretion of hydrochloric acid by 50% compared with controls.

In all the above reported tests, the activity of the compounds of the present invention has been compared with the activity of Cimetidine, well-known drug having anti-ulcer and anti-secretory activity and the relevant ED50 in the various tests are indicated in Table 2.

The anti-ulcer and anti-secretory activity of the compounds object of the present invention probably develops through a mechanism of action different from that of Cimetidine, as the compounds of the present invention differently from Cimetidine do not antagonize histamine activity at the level of $H_2$ receptors of histamine.

TABLE 2

| Compound | Cold and restraint gastric ulcers ED50 mg/kg/ os | Acetylsalicylic acid and pylorus ligation gastric ulcers ED50 mg/kg i.d. | Indomethagastric ulcers ED50 mg/kg os | Shay rats total acidity ED50 mg/kg i.d. |
| --- | --- | --- | --- | --- |
| Ia | 2,8 | 7,3 | 3,4 | 1,8 |
| Ib | 1,5 | 2,1 | 0,7 | 1,1 |
| Ic | 1,9 | 5,7 | 3,3 | 2,8 |
| Id | 0,7 | 0,9 | 0,9 | 0,6 |
| CIMEDIDIME | 6,3 | 3,8 | 2,4 | 0,6 |

The acute toxicity of the compounds of the present invention is very low both in the rat and in the mouse. In both animal species the compounds object of the present invention did not cause mortality even if administered at high doses of 1600 mg/kg orally. The compounds of the present invention can be employed in human therapy.

The oral daily dose varies between mg 200 and mg 1200 and can be administered in the form of tablets, s.c. tablets, capsules or syrup. Hereunder we are giving some examples of pharmaceutical compositions.

| Capsule formula: | |
| --- | --- |
| Compound of formula I | mg 200 |
| Lactose | mg 100 |
| Syrup formula: | |
| Compound of formula I | mg 2000 |
| aromatic syrup | ml 100 |

The following example illustrates the invention without limiting in any way its importance.

EXAMPLE

G 7 (0,023 moles) of N-cyano-N'-[2-[[(Imidazo[1,2-a]pyridin-3-yl)methyl]thio]ethyl]-S-methyl isothiourea (II in which R-$R_1$=H) are dissolved in ml 60 of methylamine. Ml 35 of 40% dimethylamine aqueous solution are added and the mixture is left resting at room temperature for 12 hours. The solvent is evaporated at reduced pressure, the residual oil is mixed with water and rapidly agitated to obtain the complete solidification of the oily dispersed drops. It is filtered and crystallized from ethanol obtaining g 4,45 (67% yield) of N-cyano-N'-methyl-N''-[2-[[imidazo[1,2-a]pyridin-3-yl)methyl]thio]ethyl]guanidine, having a M.P. of 185°–187°.

By a similar procedure, using the reaction and crystallization solvents indicated in Table 1, we obtain the other products of formula I, object of the present invention.

What we claim is:

1. An imidazo[1,2-a]pyridine of the formula

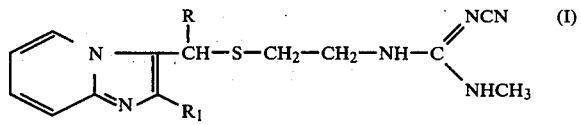

where R represents H or $CH_3$ and $R_1$ represents H or $CH_3$.

2. N-cyano-N'-methyl-N''-[2-[[(imidazo[1,2-a]pyridin-3-yl)methyl]thio]ethyl]guanidine.

3. N-cyano-N'-methyl-N''-[2-[[(2-methyl-imidazo[1,2-a]pyridin-3-yl)methyl]thio]ethyl]guanidine.

4. N-cyano-N'-methyl-N''-[2-[[1-(imidazo[1,2-a]pyridin-3-yl)-ethyl]thio]ethyl]guanidine.

5. N-cyano-N'-methyl-N''-[2-[[1-(2-methyl-imidazo[1,2-a]pyridin-3-yl)-ethyl]thio]ethyl]guanidine.

6. Pharmaceutical composition useful for the treatment of gastric hypersecretion including an effective amount of a compound of claim 1 associated with a non-toxic carrier or diluent.

* * * * *